United States Patent [19]

Nishino et al.

[11] Patent Number: 5,144,945

[45] Date of Patent: Sep. 8, 1992

[54] PORTABLE OXYGEN-ENRICHING AIR INHALER

[75] Inventors: Seigou Nishino; Masato Kawai; Kiyoshi Ohno, all of Kanagawa; Seiichi Ito, Tokyo; Nobuyoshi Itoh, Kanagawa, all of Japan

[73] Assignee: Nippon Sanso Kabushiki Kaisha, Tokyo, Japan

[21] Appl. No.: 509,842

[22] Filed: Apr. 17, 1990

[30] Foreign Application Priority Data

Apr. 20, 1989 [JP] Japan .................. 1-46397[U]
May 18, 1989 [JP] Japan .................. 1-57454[U]
Jun. 8, 1989 [JP] Japan .................. 1-67169

[51] Int. Cl.⁵ .................. A62B 7/10; A62B 19/00; A62B 23/02; A62B 18/02
[52] U.S. Cl. .................. 128/205.12; 128/205.25; 128/205.11; 128/204.15; 128/204.17
[58] Field of Search .................. 128/204.18, 205.11, 128/205.12, 205.25, 204.15, 204.17

[56] References Cited

U.S. PATENT DOCUMENTS

| D. 185,634 | 7/1959 | Fegan et al. | 128/204.15 |
|---|---|---|---|
| 2,378,468 | 6/1945 | Deming | 128/205.11 |
| 3,794,072 | 2/1974 | Diedrich et al. | 128/205.11 |
| 3,850,171 | 11/1974 | Ball et al. | 128/205.11 |
| 3,977,432 | 8/1976 | Vidal | 128/205.11 |
| 4,020,834 | 5/1977 | Bird | 128/205.12 |
| 4,561,287 | 12/1985 | Rowland | 128/205.11 |
| 4,576,616 | 3/1986 | Mottram et al. | 128/205.12 |
| 4,627,860 | 12/1986 | Rowland | 128/205.12 |
| 4,826,510 | 5/1989 | McCombs | 128/204.18 |

FOREIGN PATENT DOCUMENTS

0346566  12/1989  European Pat. Off. ....... 128/205.11

Primary Examiner—Edgar S. Burr
Assistant Examiner—Kimberly L. Asher
Attorney, Agent, or Firm—Lowe, Price, LeBlanc & Becker

[57] ABSTRACT

An oxygen rich air inhaler for use in stress relief and fatigue recovery has a casing, an inlet duct and an exhaust duct. The casing is separated into a compressor chamber and an adsorber chamber by a partition. The inlet duct has an inlet open to an end wall on the side of the adsorber chamber and provided at an upper portion of the adsorber chamber so as to communicate with the compressor chamber. The exhaust duct has an exhaust outlet open to an end wall on the side of the adsorber chamber and provided at a lower portion of the adsorber chamber so as to communicate with the compressor chamber. A suction fan and at least one compressor are disposed in the compressor chamber. At least two adsorbers, which communicate with the compressor via a selector valve, and an oxygen rich air tank, communicating air outlets of the adsorbers, are disposed in the adsorber chamber. An air inlet for the compressor and an exhaust outlet for air desorbed from the adsorbers are disposed downstream of the compressor chamber. An inhalation mask communicates with oxygen rich air tank for inhaling oxygen rich air.

5 Claims, 10 Drawing Sheets

PORTABLE OXYGEN-ENRICHING AIR INHALER

BACKGROUND OF THE INVENTION

1. Field of the Invention

The present invention generally relates to an oxygen rich air inhaler. More particularly, this invention relates to an oxygen rich air inhaler simple to use for relieving stress or recovering from weariness or fatigue.

2. Description of the Related Art

Recently, it is said that breathing or inhaling air with high oxygen density (oxygen rich air) is good for stress relief and fatigue recovery.

There is an oxygen rich air producing apparatus known which is equipped with a compressor and an adsorber, and introduces air compressed by the compressor into the adsorber, then permits an adsorbent in the adsorber to adsorb part of nitrogen to thereby acquire oxygen rich air.

Being relatively large, this air producing apparatus is effective for industrial use but not suitable for use closely associated with daily life, such as stress relief and fatigue recovery.

In this respect, the stress relief and fatigue recovery are normally done using an oxygen inhaler utilizing oxygen gas or oxygen rich air filled in a small compressed-gas cylinder, a spray type oxygen inhaler having a low-pressure oxygen rich air filled in a can, or a medicine-using oxygen inhaler.

However, the first oxygen inhaler using a compressed-gas cylinder needs replacement of the cylinder and skill to handle the container due to high pressure. The spray type is disposable and contains a less amount of oxygen rich air filled therein. The last type using a medicine is troublesome to use as it requires such a medicine to be put in water upon each usage and should have the water cast off after usage.

SUMMARY OF THE INVENTION

Accordingly, it is an object of this invention to provide an oxygen rich air inhaler, which utilizes oxygen rich air generating means having an industrially-used compressor and an adsorber to eliminate the trouble of replacing a gas cylinder, and is easy to handle as well as portable.

To achieve this object, according to the present invention, there is provided an oxygen rich air inhaler comprising:

a casing separated into a compressor chamber and an adsorber chamber by a partition;

an inlet duct having an inlet open to an end wall on a side of the adsorber chamber and provided at an upper portion of the adsorber chamber so as to communicate with the compressor chamber;

an exhaust duct having an exhaust outlet open to an end wall on the side of the adsorber chamber and provided at a lower portion of the adsorber chamber so as to communicate with the compressor chamber;

a suction fan disposed in the compressor chamber;

at least one compressor disposed in the compressor chamber;

at least two adsorbers disposed in the adsorber chamber and communicating via a selector valve with the compressor;

an oxygen rich air tank disposed in the adsorber chamber and communicating with outlets of the adsorbers;

an air inlet for the compressor;

an exhaust outlet for gas desorbed from the adsorbers, the exhaust outlet and air inlet being disposed downstream of the suction fan in the compressor chamber; and an inhalation mask communicating with the oxygen rich air tank.

With the above arrangement, air (outside air) is introduced into the compressor chamber from the inlet duct by the suction fan, the air is compressed by the compressor and led to one of the adsorbers via the selector valve to adsorb part of nitrogen contained in the air in that adsorber, and oxygen rich air acquired from the outlet of the adsorber is spouted from the inhalation mask through the oxygen rich air tank.

When adsorption of nitrogen in the adsorber progresses and approaches a saturation state, the selector valve is switched to introduce compressed air into the other adsorber, desorption and exhaustion of the adsorber in which nitrogen adsorption has reached the saturation state are executed while adsorption is being carried out in the other adsorber, and the desorbed exhaust gas is discharged through the exhaust duct out of the casing from the exhaust outlet.

When nitrogen adsorption in the other adsorber approaches the saturation state, the selector valve is again switched and adsorption in the adsorber whose desorption has been completed is executed while desorption and exhaustion of the other adsorber in which nitrogen is in the saturated state are executed.

As described above, periodic switching of the selector valve alternately switches the adsorption and desorption of each adsorber and ensures a continuous operation which can provide oxygen rich air that is to be inhaled via the inhalation mask.

The present oxygen rich air inhaler, as described above, has the inlet duct, exhaust duct, compressor chamber and adsorber chamber reasonably and properly defined within the casing, so that the cooling coil and compressor which become hot due to the compressing heat can be cooled down, thus preventing the temperature in the casing from rising. The prevention of the temperature rise can effectively prevent reduction in the adsorption efficiency of the adsorber, which may otherwise be caused by such a temperature rise, so as to generate an abundant amount of oxygen rich air, and can ensure the continuous operation. Further, the above described structure makes the present device compact and easy to carry and use, so that the device can be carried in sport establishments for quick recovery of fatigue or carried home or in an office for effective use in stress relief as well as fatigue recovery.

BRIEF DESCRIPTION OF THE DRAWINGS

FIGS. 1 through 4 illustrate one embodiment of an oxygen rich air inhaler according to the present invention, in which

FIGS. 8 through 12 illustrate one embodiment of an inhalation mask for use in the oxygen rich air inhaler, in which

DESCRIPTION OF THE PREFERRED EMBODIMENT

A preferred embodiment of an oxygen rich air inhaler according to the present invention will be described below referring to the accompanying drawings.

Figure 1:
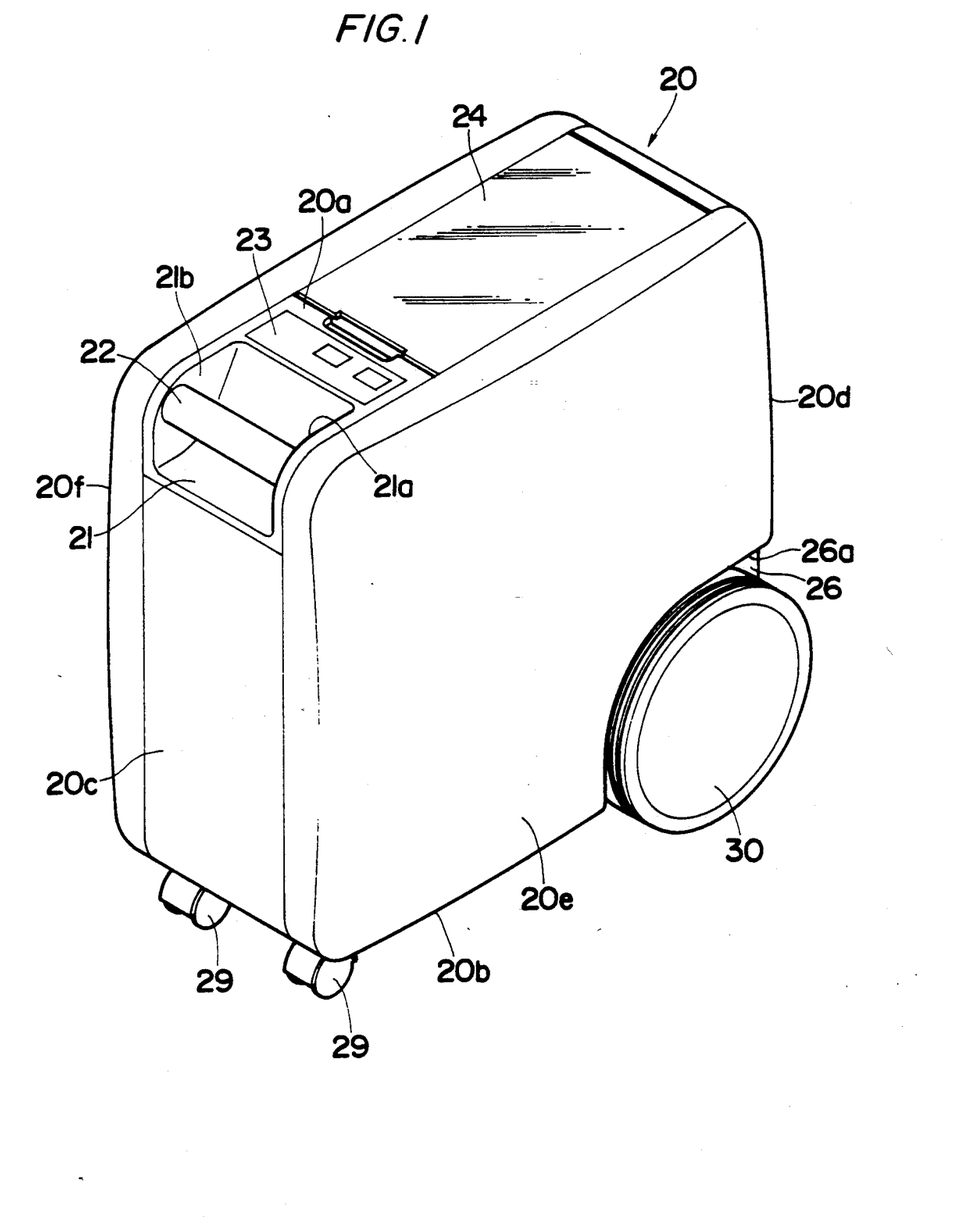
FIG. 1 is a perspective view of the inhaler.
Figure 2:
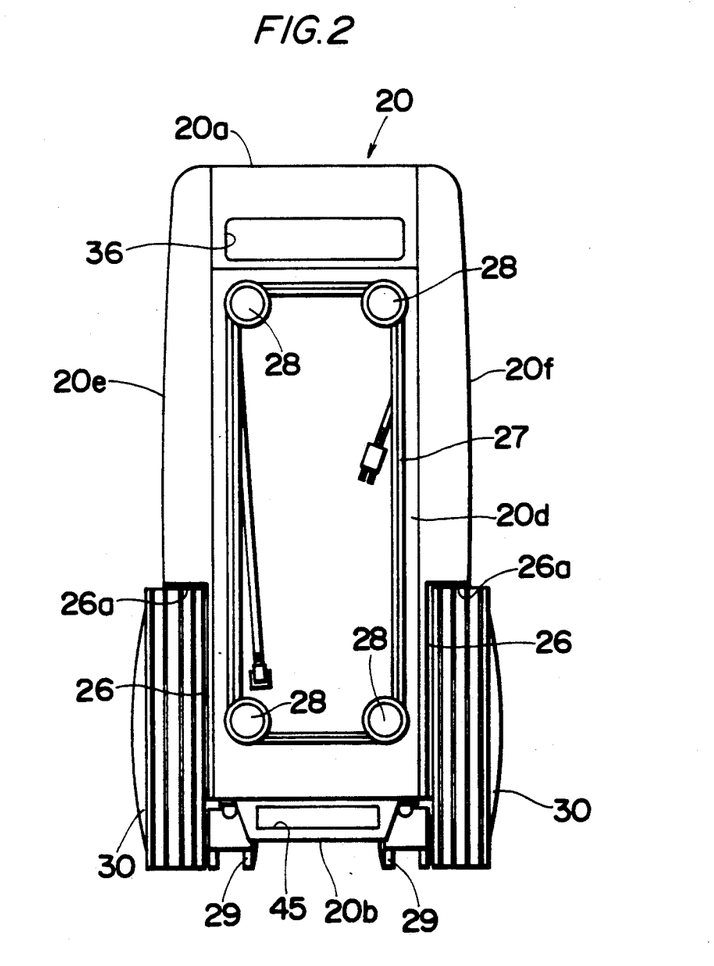
FIG. 2 is a side view thereof.
Figure 3:
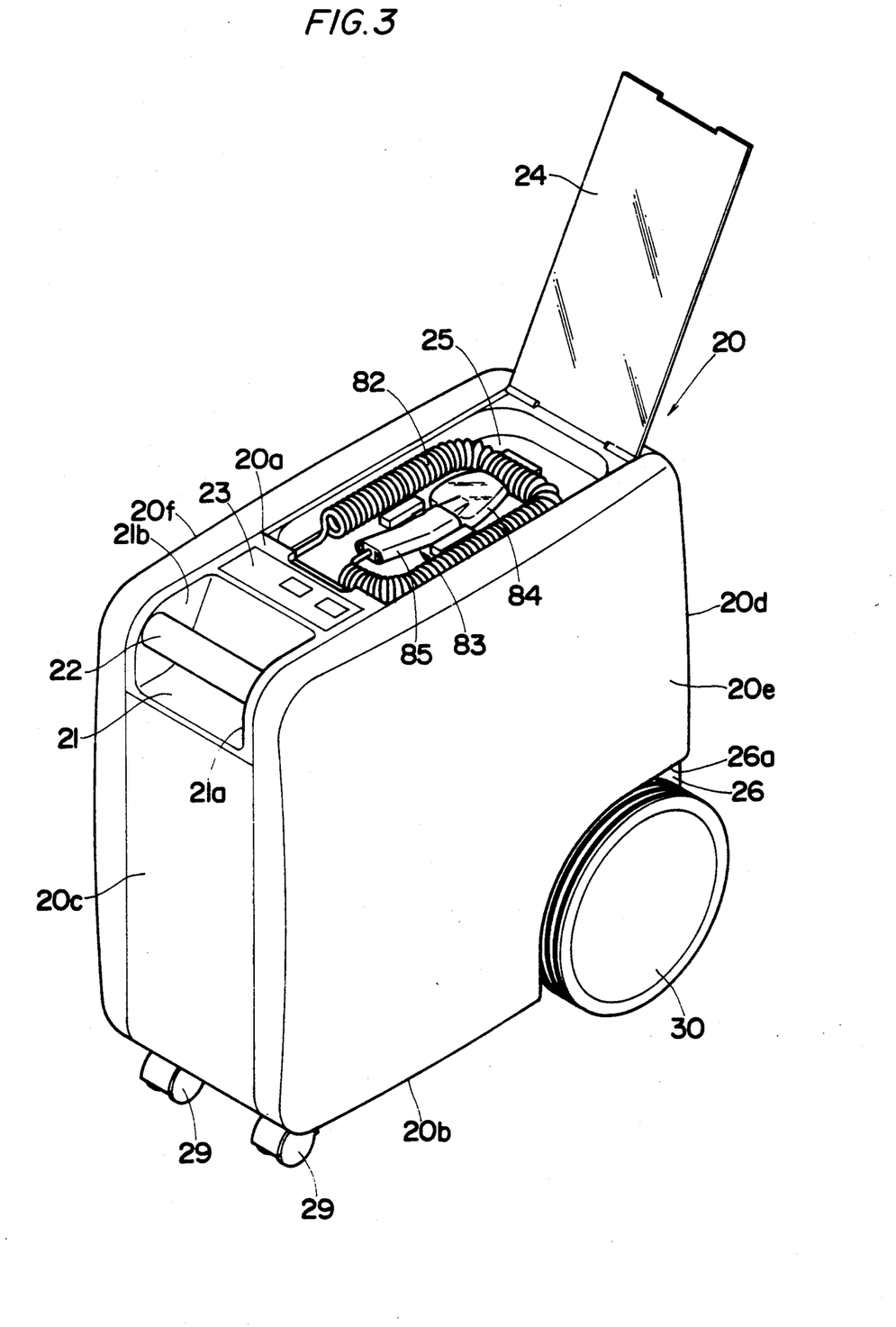
FIG. 3 is a perspective view illustrating an inhalation-mask receiving section with its lid open.
Figure 4:
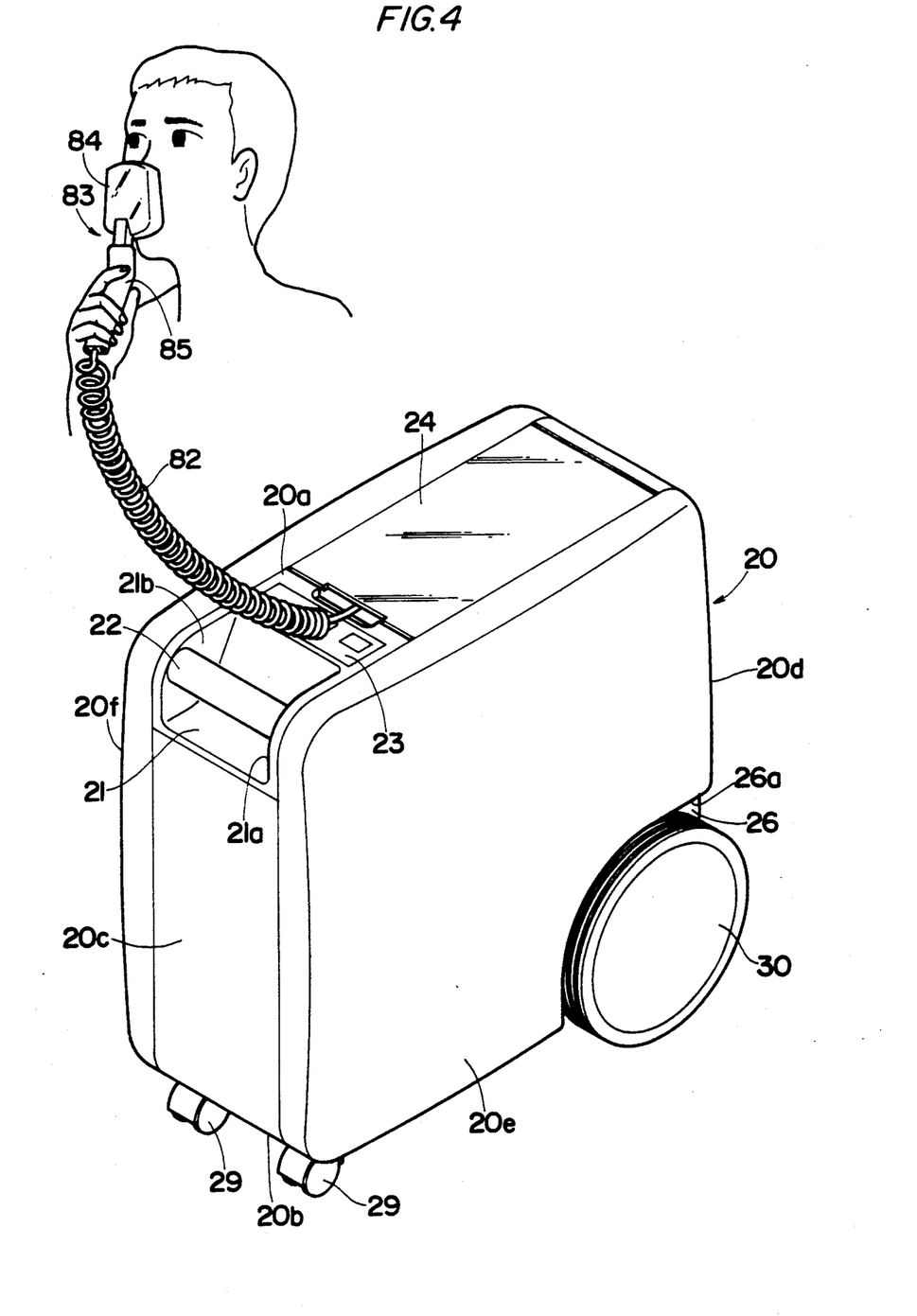
FIG. 4 is a perspective view illustrating the inhaler in use.

FIGS. 1 through 4 illustrate one embodiment of an oxygen rich air inhaler according to the present invention. FIG. 1 is a perspective view of the inhaler, FIG. 2 is a side view thereof, FIG. 3 is a perspective view illustrating an inhalation-mask receiving section with its lid open, and FIG. 4 is a perspective view illustrating the inhaler in use.

A casing 20 of the oxygen rich air inhaler is a rectangular box constituted by a top plate 20a, a bottom plate 20b, a front end wall 20c, a rear end wall 20d, side walls 20e and 20f, the last two walls being substantially higher and wider than the front and rear end walls. The side walls 20e and 20f are made slightly outwardly convex both in the horizontal and vertical directions. The casing 20 has rounded corners. A recess 21 is formed at the front upper corner of the casing 20 between the top plate 20a and front end wall 20c, with a bar 22 having both ends attached to respective side portions 21a and 21b of the recess 21 and extending across the recess 21.

On the top plate 20a are provided a switch panel 23 and a recessed inhalation-mask receiving section 25 with a lid 24 at the top.

The lower portion of each of the side walls 20e and 20f adjacent to the rear lower corner of the casing 20 is inwardly recessed to from a recess 26 with an arcuate upper edge 26a.

A power cord 27 extends outward from the rear end wall 20d and is to be wound around four projections 28 provided on the wall 20d for neat tucking of the cord.

At the lower portion of the casing 20 are provided a pair of small casters 29 and a pair of large casters 30. The small casters 29, laterally spaced from each other, are attached in a directable manner to the front portion of the bottom plate 20b at the proximity of the lower front corner of the casing 20. The large casters 30 are mounted on the respective ends of a shaft (not shown), disposed at the recesses 26 of the casing 20 and laterally penetrating the casing 20.

Figure 5:
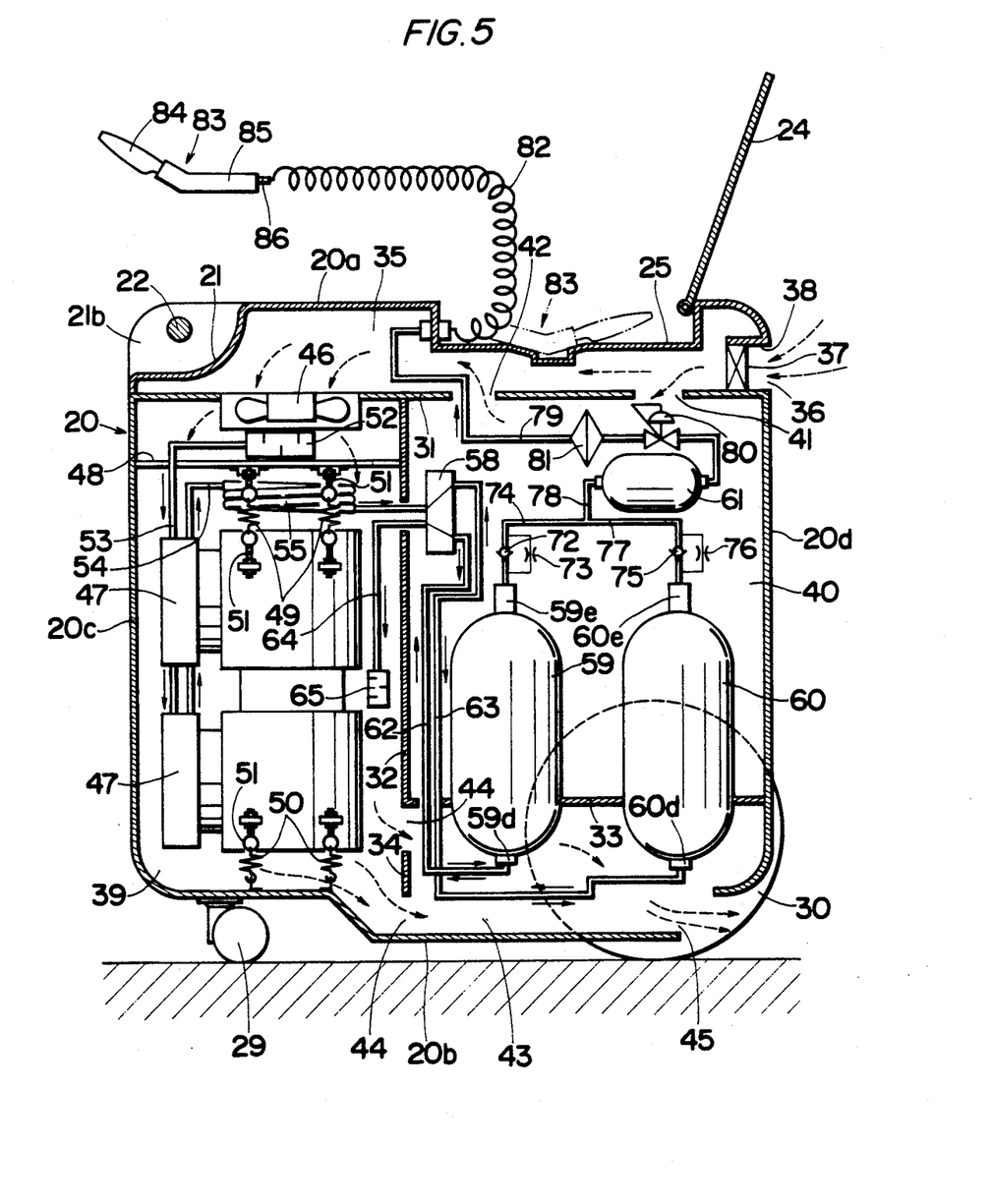
FIG. 5 is a cross section of a casing illustrating the internal structure of the oxygen rich air inhaler.

FIG. 5 is a cross section of the casing 20 and illustrates the internal structure of the oxygen rich air inhaler.

The casing 20 has inside a horizontal upper partition wall 31, a vertical center partition wall 32 and a horizontal lower partition wall 33. The upper partition wall 31 separates the inside of the casing 20 between the side walls 20e and 20f, across the upper portion of the front end wall 20c and the upper portion of the rear end wall 20d. The center partition wall 32 partitions the interior of the casing 20 also between the side walls 20e and 20f, downward from approximately the center portion of the partition wall 31. The lower partition wall 33 partitions the casing's interior between the side walls 20e and 20f, rearward from the lower end of the partition wall 32. Between the center partition wall 32 and the bottom plate 20b is disposed a reinforced wall 34 extending across the side walls 20e and 20f.

An inlet duct 35 is defined by the top plate 20a, upper partition wall 31 and side walls 20e and 20f. An inlet 36 of the inlet duct 35 is formed in the rear end wall 20d. The inlet 36 is provided with a filter 37. An upper stepped portion 38 of the inlet 36 serves as a handle for carrying the present device.

A compressor chamber 39 is defined by the front end wall 20c, bottom plate 20b, upper partition wall 31, center partition wall 32, and side walls 20e and 20f.

An adsorber chamber 40 is defined by the upper partition wall 31, center partition wall 32, lower partition wall 33, rear end wall 20d and side walls 20e and 20f. In the upper partition wall 31 are formed open an air inlet 41 and air outlet 42, through which part of air introduced into the inlet duct 35 from the inlet 36 is led into, and discharged from, the adsorber chamber 40.

An exhaust duct 43 is defined by the lower partition wall 33, bottom plate 20b and side walls 20e and 20f. This duct 43 communicates with the compressor chamber 39 via top and bottom openings 44 bored in the reinforced wall 34, and has an air outlet 45 formed open in the rear end wall 20d.

A suction fan 46 is provided at that portion of the upper partition wall 31 which corresponds to the compressor chamber 39, to suck air from the inlet duct 35 in the compressor chamber 39.

Two compressors 47 are serially connected and disposed in the compressor chamber 39. The compressors 47 are suspended by springs 49 and 50 between a beam 48 located above the compressors 47 and the bottom plate 20b. More specifically, the compressors 47 have their tops hung from the beam 48 by the four springs 49, and their bottoms flexibly supported on the bottom plate 20b by the four springs 50, so that vibration during operation of the compressors 47 is not transmitted to the casing 20 and the other components within the casing 20 as much as possible and noise caused by driving the compressors is reduced. The resilient force of each of the springs 49 and 50 is controlled by adjusting the fastening of eye bolts 51 that hold the springs 49 and 50. Although two compressors 47 are employed in this embodiment, the quantity is not limited to two but at least one compressor is sufficient to realize the present invention.

An air inlet 52 of the compressors 47 is provided directly under the suction fan 46 or downstream of the suction fan 46, and connects to the upper compressor 47 via a suction pipe 53.

Figure 6:
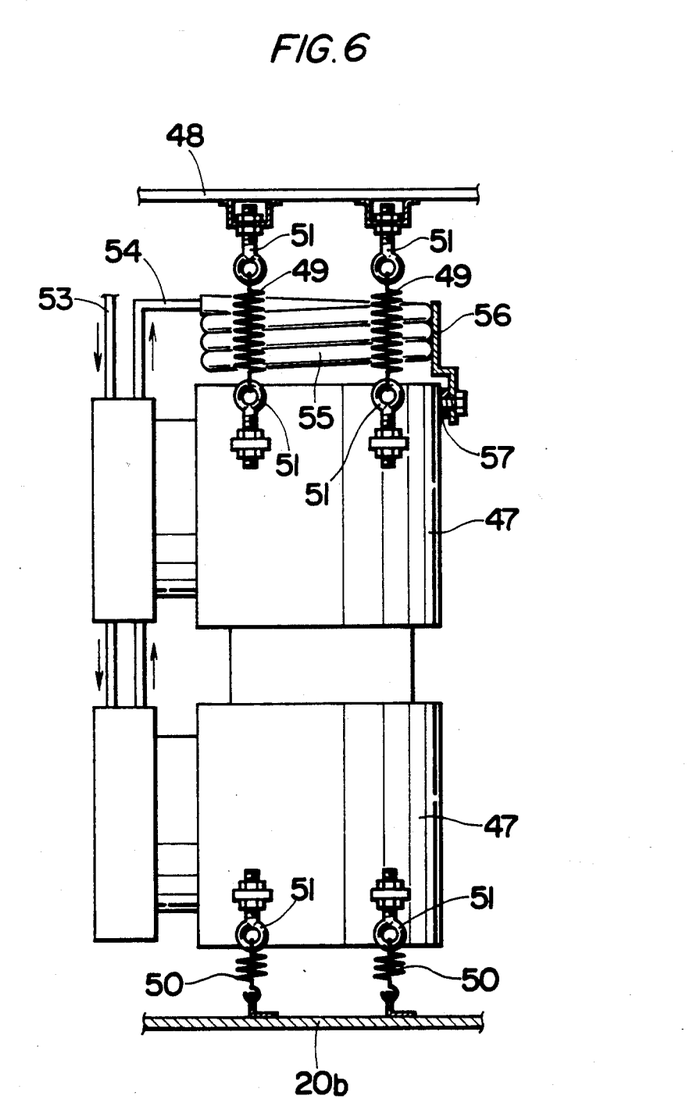
FIG. 6 is a front view of compressor-supporting means.

A cooling coil 55 connecting via a discharge pipe 54 to the upper compressor 47 is disposed between the air inlet 52 and the upper compressor 47, and is supported on the upper compressor 47 through a fixing member 56 and rubber bushes 57, as shown in FIG. 6. Accordingly, air compressed by the compressors 47 is cooled at the cooling coil 55 by an air stream going from inside the compressor chamber 39 to the exhaust duct 43.

In the adsorber chamber 40 are provided a selector valve 58, two adsorbers 59 and 60 and an oxygen rich air tank 61. The selector valve 58 communicates with the cooling coil 55 and also with air inlets 59d and 60d at the lower portions of the adsorbers 59 and 60 via conduits 62 and 63. The selector valve 58 further communicates via a conduit 64 with an exhaust outlet 65 provided in the compressor chamber 39.

The selector valve 58 is a five-way electromagnetic valve, which is switched by a timer or a pressure switch to select supply of compressed air to the adsorber 59 or 60 and select between desorption and exhaustion of nitrogen or the like adsorbed in the adsorbers 59 and 60.

Figure 7:
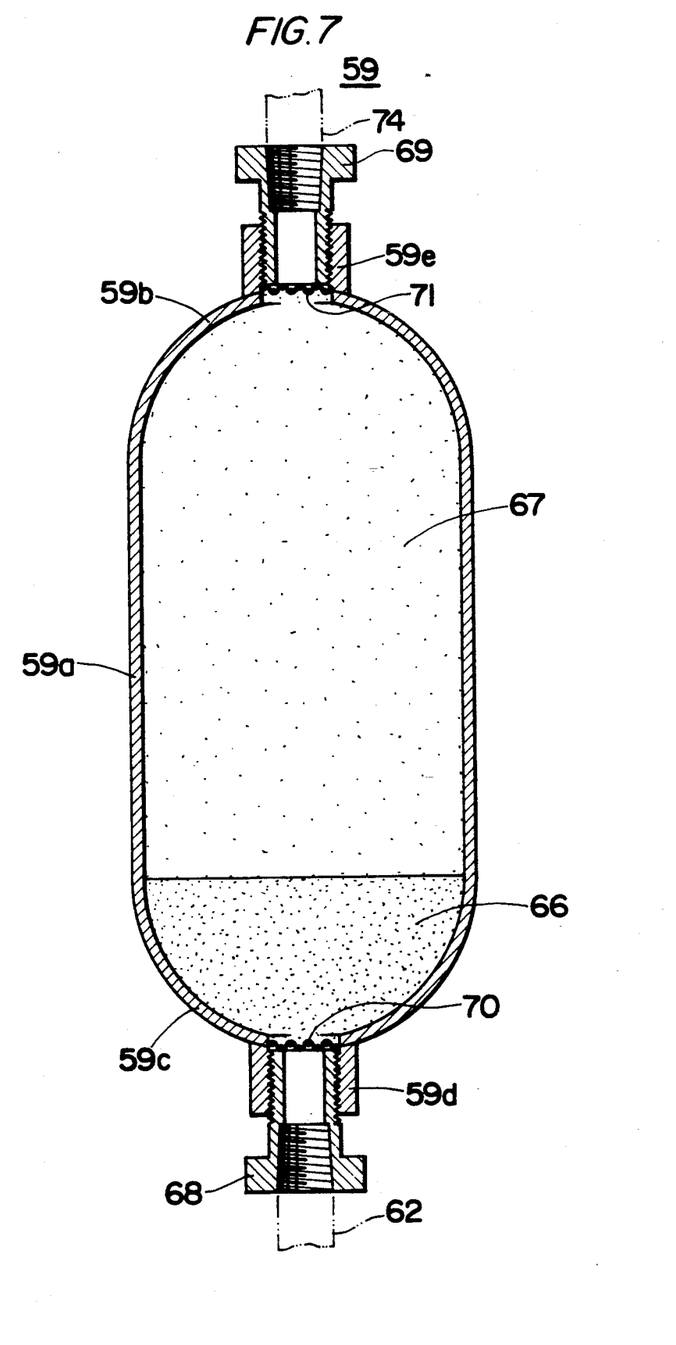
FIG. 7 is a cross section of an adsorber.

As the adsorbers 59 and 60 have the same structure, the adsorber 59 will be described in more detail referring to FIG. 7.

The adsorber 59 is filled at the lower portion with a desiccant 66 and at the upper portion with an adsorbent 67, such as zeolite, which adsorbs nitrogen.

The adsorber 59 comprises a cylindrical body portion 59a, an upper cap portion 59b and a lower cap portion 59c, the latter two having a semicircular shape and constituting the upper and lower end portions, respectively. The lower cap portion 59c and upper cap portion 59b have an inlet 59d and an outlet 59e formed in the top portions along the axis of the adsorber 59.

The inlet 59d and outlet 59e are respectively engaged with pipe joints 68 and 69 which connect to conduits for air inlet and outlet. It is preferable that the diameter of each of the pipe joints 68 and 69 is within a range greater than at least 1/10 of the inner diameter of the body portion 59a and less than ⅓ thereof. This size permits air flowing in the adsorber 59 to uniformly flow across the adsorber 59 in the lateral direction.

Leak preventing members 70 and 71, which have minute perforations smaller than the diameter of particles of the desiccant 66 and adsorbent 67 filled in the adsorber 59, are respectively provided at the inner end portions of the pipe joints 68 and 69 in the inlet 59d and outlet 59e.

The leak preventing members 70 and 71 each may be a porous plate, a metal mesh, a porous filter, a sintered metal, a porous ceramic, or a honeycomb member, or may be made of a calcium silicate or the like.

In filling the thus structured adsorber 59 with an adsorbent or the like, for example, after the pipe joint 68 and leak preventing member 70 are attached to the inlet 59d and the desiccant 66 and adsorbent 67 are filled in the adsorber 59 from the outlet 59e, the pipe joint 69 and leak preventing member 71 are attached to the outlet 59e.

At this time, the leak preventing members 70 and 71 permit the filled desiccant 66 and adsorbent 67 to be held in the adsorber 59 without leaking outside.

To ensure an adsorption operation in the adsorber 59, when compressed air is introduced in the adsorber 59 from the outlet 59d, gas uniformly flows in the adsorber 59 toward the outlet 59e by the semicircular face of the lower cap portion 59c.

Therefore, the desiccant 66 and absorbent 67 can be filled in the entire interior of the adsorber 59 and the entire volume of the adsorber 59 can be used as an adsorption effective space, so that the present device is significantly effective and the adsorber can be made compact.

The lower portions of the adsorbers 59 and 60 or those portions which are filled with the desiccant 66 protrude from the lower partition wall 33 and extend into the exhaust duct 43.

A conduit 74 having a check valve 72 and an orifice 73 bypassing the valve 72 is connected to the outlet 59e of the adsorber 59, while a conduit 77 having a check valve 75 and an orifice 76 bypassing the valve 75 is connected to the outlet 60e of the adsorber 60. Both conduits 74 and 77 merge together to form a conduit 78 before the oxygen rich air tank 61, conduit 78 being connected to the tank 61.

A pressure regulating valve 80 and a filter 81 are provided at an outlet conduit 79 of the oxygen rich air tank 61, and the conduit 79 protrudes into the inhalation-mask receiving section 29 formed in the top plate 20a from the side wall of the section 29. The end portion of the connected portion of the outlet conduit 79 that protrudes in the receiving section 25 communicates with an inhalation mask 83 through a helically coiled tube 82.

The tube 82 and inhalation mask 83, when not in use, are accommodated in the receiving section 25, as shown in FIG. 3, and are taken out from there when in use as shown in FIG. 4.

Figure 8:
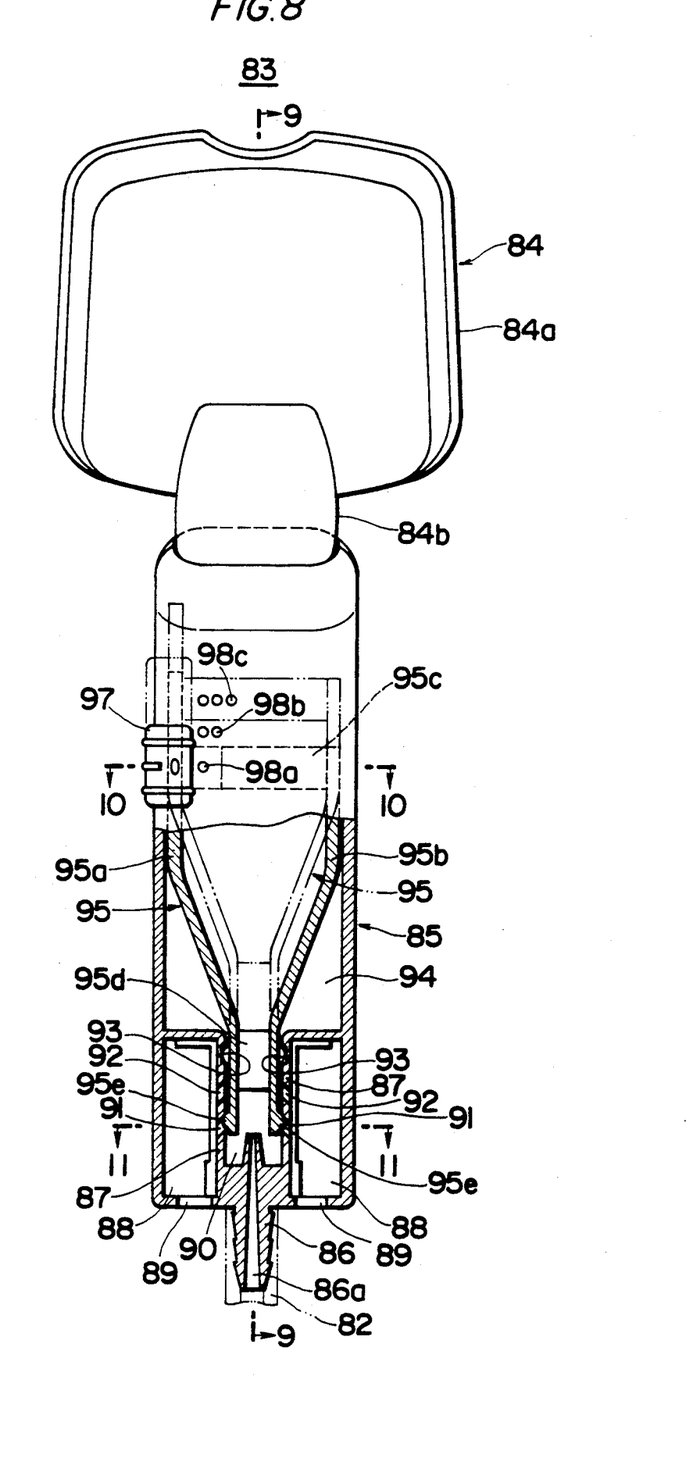
FIG. 8 is a partly cutaway front view.
Figure 9:
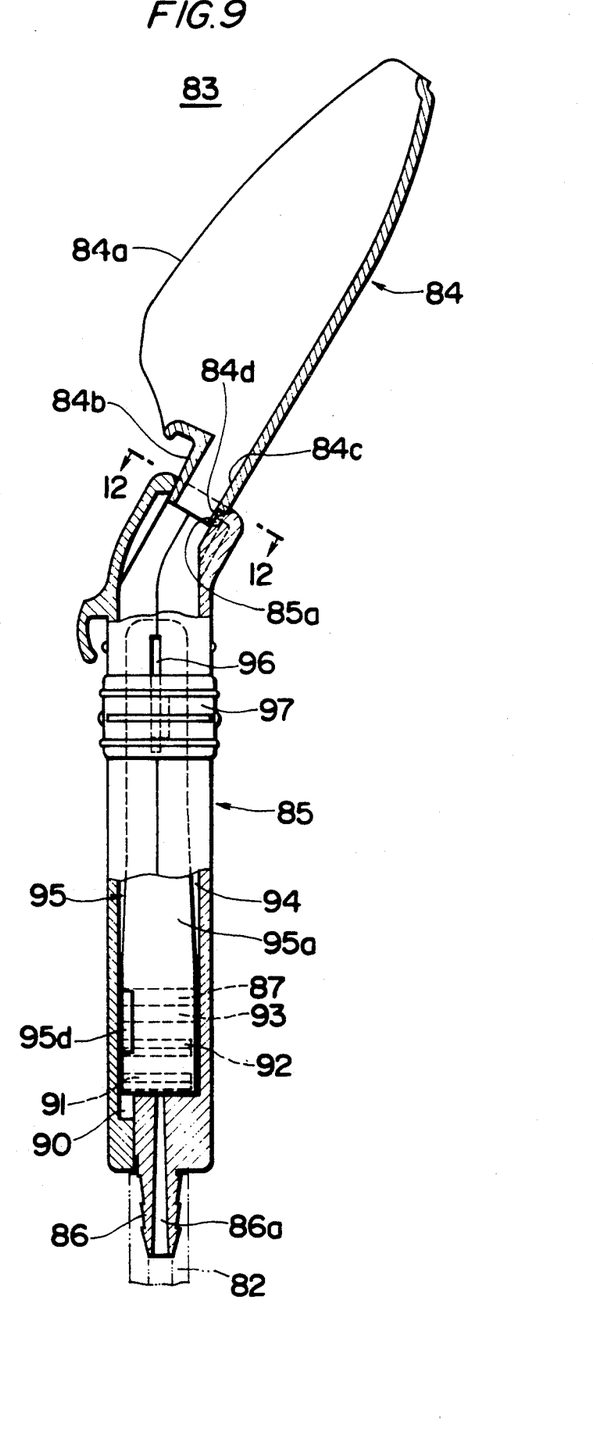
FIG. 9 is a cross section taken along the line 9—9 in FIG. 8.
Figure 10:
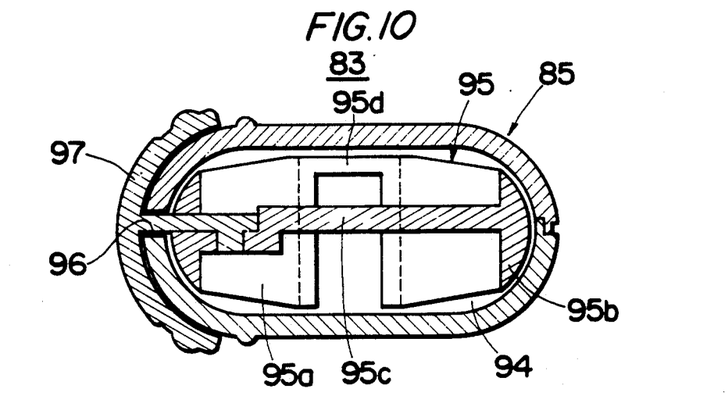
FIG. 10 is a cross section taken along the line 10—10 in FIG. 8.
Figure 11:
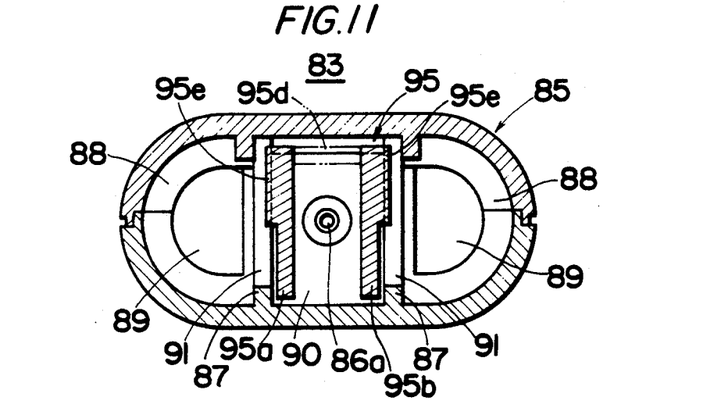
FIG. 11 is a cross section taken along the line 11—11 in FIG. 8.
Figure 12:
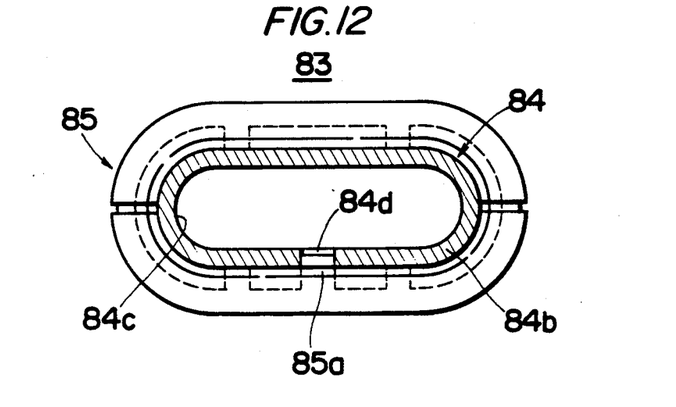
FIG. 12 is a cross section taken along the line 12—12 in FIG. 9.

FIGS. 8 through 12 illustrate one embodiment of an inhalation mask. FIG. 8 is a partly cutaway front view, FIG. 9 is a cross section taken along the line 9—9 in FIG. 8, FIG. 10 is a cross section taken along the line 10—10 in FIG. 8, FIG. 11 is a cross section taken along the line 11—11 in FIG. 8, and FIG. 12 is a cross section taken along the line 12—12 in FIG. 9.

The inhalation mask 83 has a mask portion 84 of synthetic resin and a grip portion 85. The mask portion 84 has a cover portion 84a for covering around the mouth and nose of a user and a neck portion 84b integrally formed at the lower portion of the cover portion 84a.

The grip portion 85 is a flat hollow body bent, at near the upper edge, rearward of the mask portion 84 about 30 degrees. The neck portion 84b of the mask portion 84 is fitted in the upper end of the grip portion 85 so that the portion 85 communicates with a passage 84c in the neck portion 84. A connector 86 which is to be connected with the tube 82 is protrusively provided at the lower end of the grip portion 85.

The mask portion 84 and grip portion 85 are linked together by fitting a positioning projection 84a formed at the inner portion of the upper end of the grip portion 85 into a groove 84d formed in the lower end of the neck portion 84b.

Outside air introducing chambers 88 are defined by partitions 87 in the grip portion 85 at both sides of the lower portion thereof, and communicate with the outside through outside air inlets 89 opened at the lower portion of the grip portion 85. An oxygen rich air passage 90, which communicates with an oxygen rich air inlet passage 86a bored in the connector 86, is formed between partitions 87 at the lower portion of the grip portion 85.

Slit or hole passages 91 and 92, which permit the outside air inlet chambers 88 at both sides to communicate with the center oxygen rich air passage 90, are bored in two stages with different phases in the partitions 87. Engaging recesses 93 are respectively formed in the partitions 87 over the upper-stage passages 92.

The upper portion in the grip portion 85 is a space expanding over the entire interior and forming a mixing chamber 94 in which oxygen rich air supplied from the tube 82 is mixed with the outside air. The lower portion of the mixing chamber 94 communicates with the upper portion of the narrower oxygen rich air passage 90.

An adjuster 95, which adjusts the ratio of mixing the oxygen rich air and outside air, is provided in the mixing chamber 94 and oxygen rich air passage 90 in a slidable manner in the axial direction of the grip portion 85.

The adjuster 95 has side plates 95a and 95b, an upper link member 95c and a lower link member 95d. The side plates 95a and 95b are parallel to each other at the upper portion along the inner wall of the mixing chamber 94, and become narrower to be in a taper shape and are parallel to each other the lower portion along the partitions 87. The upper link member 95c connects the upper portion of both side plates 95a and 95b. The lower link member 95d connects the lower portions of the side plates 95a and 95b. Engaging projections 95e are formed on the lower outer walls of the side plates 95a and 95b.

That portion of the adjuster 95 which moves within the oxygen rich air passage 90 serves as a valve. Movement of the adjuster 95 causes the engaging projections 95e to engage with the lower-stage air passages 91, the upper-state air passages 92 or the engaging recesses 93, so that the lower end portions of the side plates 95a and 95b serve to gate the passages 91 or 92 to thereby adjust the amount of the introduced outside air.

A notch 97 is provided at the upper portion of the adjuster 95, the notch 97 protruding outside the grip portion 85 from a longitudinally elongated hole 96 formed in the upper side wall of the grip portion 85. Scales 98a, 98b and 98c indicating the amount of the sliding movement of the adjuster 95 are provided on the outer side wall of the grip portion from which the notch 97 protrudes.

The operation of the thus constituted oxygen rich air inhaler will now be described.

First, in actual use, a user would pull the bar 22 to move the present device by rolling the casters 29 and 30 or hold the bar 22 and the upper stepped portion 38 of the inlet 36 to carry the device to the desired place.

Then, the user connects the power cord 27 to a power source, opens the lid 24 to take out the inhalation mask 83 from the receiving section 25, and throw on the main switch on the switch panel 23. As a result, the suction fan 46 and compressors 47 are driven to introduce raw air (outside air) into the upper compressor 47 from the air inlet 52, passing through the inlet 36 and the inlet duct 35. This air is compressed in multi-stages by both compressors 47 and is sent to the selector valve 58 through the discharge pipe 54 and the cooling coil 55.

At this time, that of the raw air introduced into the compressor chamber 39 by the suction fan 46 which is not led into the compressor 47 from the air inlet 52 cools the compressed air in the cooling coil 55 and the compressors 47, whose temperatures have risen due to the compressing heat, then is discharged outside the inhaler from the air outlet 45 via the exhaust duct 43. Further, part of the raw air flowing in the inlet duct 35 is led into the adsorber chamber 40 from the air inlet 41 to cool the upper portions of the adsorbers 59 and 60 and is returned to the inlet duct 35 from the air outlet 42 to thereby improve the adsorption efficiency of both adsorbers 59 and 60.

The compressed air led into the selector valve 58 is supplied to either the adsorber 59 or 60 by the switching operation of the valve 58. For instance, the compressed air sent to the adsorber 59 via the conduit 62 has part of nitrogen, one of its components, adsorbed in the adsorber 59 to form an oxygen rich air with an oxygen percentage of approximately 40% to 60%. The formed oxygen rich air is sent at a rate of about 5 l per minute into the oxygen rich air tank 61 for a reserving purpose through the conduits 74 and 78.

When a certain time elapses and adsorption of nitrogen in the adsorber 59 progresses and approaches a saturation state, the selector valve 58 is switched by the function of a timer or the like, and the compressed air from the compressor 47 is supplied via the conduit 63 to the other adsorber 60 in which air reproduction has already been completed. Part of the nitrogen is likewise adsorbed in the adsorber 60 and oxygen rich air is sent to the tank 61 via the conduits 77 and 78.

During the above process, the switching of the selector valve 58 stops the supply of compressed air to the adsorber 59, so that the adsorber 59 communicates with the exhaust outlet 65 via the conduit 62, selector valve 58 and conduit 64, thereby releasing the pressure.

As a consequence, gas consisting of nitrogen adsorbed in the adsorber 59 as its main component is desorbed and exhausted, and part of the oxygen rich air acquired by the adsorber 60 reversely flows through the orifice 73 into the adsorber 59 for air reproduction.

The gas containing the desorbed exhaust nitrogen as the main component is discharged into the compressor chamber 39 from the exhaust outlet 65, The gas is then forced out of the inhaler from the air outlet 45 via the exhaust duct 43, accompanied by part of the raw air introduced into the compressor chamber 39 by the suction fan 46.

At this time, the desorbed exhaust gas discharged into the compressor chamber 39 also cools the compressors 47 to prevent the temperature in the chamber 39 from rising and prevent the temperature rise in the adsorber chamber 40 as it is not discharged into the chamber 40, thereby effectively preventing reduction in adsorption performance of the adsorbers 59 and 60.

Because the temperature of the air discharged from the air outlet via the exhaust duct 43 has risen as the air has cooled the compressor chamber 39, it warms the desiccant 66 retained at the lower portions of the adsorbers 59 and 60 which face the exhaust duct 43, thus improving the drying performance.

When nitrogen adsorption in the adsorber 60 approaches the saturation state, the selector valve 58 is again switched, and the adsorber 59 where air reproduction has already completed executes the adsorption process while the adsorber 60 executes the desorption and exhaustion process.

Periodic switching of the selector valve 58 alternately switches the adsorption process and the desorption and exhaustion process of the adsorbers 59 and 60 to ensure a continuous operation to acquire oxygen rich air.

Further, although the compressors 47 whose temperatures would rise when driven and the adsorbers 59 and 60 whose adsorption performance would be reduced by the temperature rise are disposed in the casing 20, since the raw air sucked in the casing 20 and the desorbed exhaust gas desorbed from the adsorbers 59 and 60 would flow as described above, the temperature in the casing 20 can be prevented from rising and a sufficient adsorption performance can be maintained. This feature can contribute to making the casing 20 compact.

When the pressure in the oxygen rich air tank 61 exceeds a predetermined level, the pressure regulating valve 80 is opened so that the oxygen rich air retained in the tank 61 is sent via the filter 81, the outlet conduit 79 and the tube 82 to the inhalation mask 83. That is, the oxygen rich air supplied from the tube 82 connected to the connector 86 passes through the grip portion 85 and is injected into the cover portion 84a from the passage 84c in the neck portion 84b of the inhalation mask 84.

At this time, if the notch 97 is set down to the lowest scale 98a, the engaging projections 95e of the adjuster 95 engage with the lower-stage air passages 91 formed in the partitions 87 and the adjuster 95 closes the air passages 91 and the upper-stage air passages 92 to thereby inhibit introduction of the outside air into the mixing chamber 94 from the outside air inlet 89. Consequently, the oxygen rich air with an oxygen percentage of approximately 40% to 60% supplied from the tube 82 is inhaled as it is.

Then, moving the notch 97 to the middle scale 98b causes the adjuster 95 to slide upward, so that the engaging projections 95e engage with the upper-state air passages 92 and the lower-stage air passages 91 are opened. As a result, the outside air is introduced into the oxygen rich air passage 90 through the outside air inlet chambers 88 and air passages 91 and is sent, together with the oxygen rich air from the tube 82, into mixing chamber 94. These airs are mixed there for dilution.

Further moving the notch 97 to the upper scale 98c causes the engaging projections 95e to engage with the engaging recesses 93, opening the air passages 91 and 92. As a result, a large amount of outside air flows in and further dilutes the oxygen rich air supplied from the tube 82.

In this manner, the oxygen percentage can be diluted to approximately 25% by the oxygen percentage adjusting mechanism provided at the inhalation mask 83.

When the user operates the notch 97 while covering the mouth and nose with the mask portion 84 and holding the grip portion 85, as shown in FIG. 4, therefore, the density of oxygen inhaled through the inhalation mask 83 can be easily changed while using the present device. For instance, if the air with an oxygen percentage of 40% and supplied at a rate of 5 l per minute from the oxygen rich air tank 61 is adjusted by the inhalation mask 83 to have 25% oxygen, the rate of injected air becomes 38 l per minute, thus providing a significant rate of air flow and a significant feeling of using the present device.

Therefore, the user can easily select the proper or desired rate of air flow and oxygen percentage and inhale the selected rate of air with the selected oxygen percentage.

The oxygen rich air tank 61 can be made compact by permitting the inhalation mask 83 to dilute the oxygen rich air acquired in the adsorbers 59 and 60 at the time the present device is used.

As the oxygen rich air inhaler according to this embodiment produces oxygen rich air in the above manner, an abundant amount of oxygen rich air can be produced and a continuous operation is possible. In addition, in the embodiment, the overall weight of the present device is reduced to about 25 kg and the casing 20 can be made compact to have a size of 270 mm×525 mm×505 mm, so that this inhaler is easy to carry and use.

Accordingly, the present device can be carried in sport establishments, such as on a bench on a baseball field, in a locker room on a field or on the filed itself, for quick recovery of fatigue, or can be carried home or in an office for effective use in health improvement, such as stress relief and fatigue recovery.

It should be noted that providing a plurality of connecting portions of the outlet conduit 79 to the tube 82 can permit connection of a plurality of inhalation masks. Further, the oxygen percentage adjusting mechanism provided at the inhalation mask may be provided on the casing.

What is claimed is:

1. An oxygen rich air inhaler comprising:
   a casing separated into a compressor chamber and an adsorber chamber by a partition;
   an inlet duct having an inlet open to an end wall of said casing on a side of said adsorber chamber and provided at an upper portion of said adsorber chamber so as to communicate with said compressor chamber;
   an exhaust duct having an exhaust outlet open to an end wall of said casing on said side of said adsorber chamber and provided at a lower portion of said adsorber chamber so as to communicate with said compressor chamber;
   a suction fan disposed in said compressor chamber;
   at least one compressor suspended by a spring in said compressor chamber, said compressor chamber including a cooling coil for air compressed by said compressor;
   at least two adsorbers, each said adsorber communicating via a selector valve with said compressor;
   means for warming lower portions of said adsorbers, said means for warming further comprising openings in said adsorber chamber to permit a lower portion of each adsorber to extend into said exhaust duct such that each said lower portion of each said adsorber is warmed by air passing through said exhaust duct;
   an oxygen rich air tank disposed in said adsorber chamber and communicating with outlets of said adsorbers;
   an air inlet for said compressor;
   an exhaust outlet for gas desorbed from said adsorbers, said exhaust outlet and air inlet being disposed downstream of said suction fan in said compressor chamber; and
   an inhalation mask communicating with said oxygen rich air tank;
   said inlet duct further comprising means for cooling said upper portion of each said adsorber, said means for cooling further comprising an inlet portion and an outlet portion in said inlet duct for permitting part of air introduced from said inlet flow in said adsorber chamber and cool said upper portions.

2. An oxygen rich air inhaler according to claim 1, wherein said casing has casters at a lower portion thereof.

3. An oxygen rich air inhaler according to claim 1, wherein each of said adsorbers has a top cap portion and a bottom cap portion formed into a semicircular shape, has an air outlet and an air inlet formed in center portions of said top and bottom cap portions, respectively, and has leak preventing members provided at said air outlet and air inlet for preventing leakage of an adsorbent in each of said adsorbers.

4. An oxygen rich air inhaler according to claim 1, wherein a receiving section for said inhalation mask is formed at an upper portion of said casing.

5. An oxygen rich air inhaler according to claim 1, wherein said inhalation mask has a grip portion and a mask portion communicating with said grip portion, said grip portion having an interior divided into an oxygen rich air passage communicating with said mask portion and an outside air inlet chamber by a partition having a plurality of air passages formed therein, said inhalation mask further including an adjuster slidable on said partition to open and close said air passages, said adjuster being provided in said grip portion, and a notch for operating said adjuster, said notch protruding outside said grip portion.

* * * * *